United States Patent [19]

Gaffar

[11] 4,165,368
[45] Aug. 21, 1979

[54] DENTAL PROPHYLACTIC PASTE

[75] Inventor: Maria C. Gaffar, Somerset, N.J.

[73] Assignee: Colgate Palmolive Company, New York, N.Y.

[21] Appl. No.: 968,716

[22] Filed: Dec. 11, 1978

Related U.S. Application Data

[63] Continuation-in-part of Ser. No. 812,030, Jul. 1, 1977, Pat. No. 4,143,126.

[51] Int. Cl.$^2$ .............................................. A61K 7/18
[52] U.S. Cl. ...................................... 424/52; 424/49; 424/151; 424/152
[58] Field of Search .................................. 424/49–58, 424/151, 152

[56] References Cited

U.S. PATENT DOCUMENTS

| | | | |
|---|---|---|---|
| 3,228,845 | 1/1966 | Najjar | 424/49 |
| 3,257,282 | 6/1966 | Muhler | 424/52 |
| 3,337,412 | 8/1967 | Elbreder | 424/151 |
| 3,892,843 | 7/1975 | Muhler et al. | 424/52 |

*Primary Examiner*—Shep K. Rose
*Attorney, Agent, or Firm*—Robert L. Stone; Murray M. Grill; Herbert S. Sylvester

[57] ABSTRACT

A dental prophylactic paste comprising an abrasive, a humectant, gelatin alone or in combination with silica gel or a water soluble silicate and optional flavoring and preservative ingredients having a viscosity in the range of 1200–150,000 centipoises at about 30°–40° C. which possesses improved flowability by which the paste can be poured through a nozzle under low pressure into individual containers as well as improved non-spatterability and cleaning efficiency in use by the dentist.

12 Claims, No Drawings

DENTAL PROPHYLACTIC PASTE

This application is a continuation-in-part of my co-pending application Ser. No. 812,030 filed July 1, 1977 now U.S. Pat. No. 4,143,126, granted Mar. 6, 1979, relates to prophylactic dental pastes used by dentists in the periodic cleaning of teeth, now U.S. Pat. No. 4,143,126.

The primary object of the invention is to provide a prophylactic dental paste with good flowability properties so that the same can be poured into individual containers through a nozzle with a minimum of pressure, is substantially non-spattering and has improved cleaning efficiency in use by the dentist.

The foregoing object is accomplished by providing a composition comprising an abrasive, a humectant and gelatin alone or in combination with silica gel or a water-soluble silicate with optional ingredients such as flavoring agents, preservatives and the like wherein the viscosity of the paste is in the range of 1200 to 150,000 centipoises at about 30°–40° C.

Applicant has discovered that by using gelatin instead of agar-agar in a range by weight of about 0.01 to 10%, preferably about 1–5%, and abrasives in a range by weight of about 30–80%, preferably about 40–60%, a paste is provided having a viscosity range of 1200 to 150,000 centipoises at about 30°–40° C. whose characteristics of flowability and non-spatterability are improved.

The gelatin which is employed in the instant prophylactic dental paste may be Type A having a gel strength of 75–350 Bloom gms. or Type B having a gel strength of 75–250 Bloom gms. as described in the publication "Gelatin" prepared and published by the Gelatin Manufacturers Institute of America, Inc., 516 Fifth Ave., New York, N.Y., Copyright 1973, which is herein incorporated by reference.

Although the preferred abrasive is medium and fine grade pumice, other abrasives can be used such as hard minerals (Mohs hardness of 5 to 9), for example, silica, silicates such as calcium silicate, zirconium silicate, topaz, feldspar, talcs, diatomaceous silica, alumina, titanium dioxide and ferric titanate, etc., and softer minerals (Mohs hardness below 5), for example, the phosphates such as $CaHPO_4$, $CaHPO_4 \cdot 2H_2O$, $Ca_2P_2O_7$, $Ca_3(PO_4)_2$, and sodium metaphosphate as well as gypsum, apatite, calcite, etc.

The prophylactic dental paste also includes a humectant and, while the preferred humectant in the instant composition is glycerin, glycols may be used as well, such as ethylene glycol, propylene glycol and the like. In those pastes which contain water, the humectant content can be about 15–45% by weight, preferably 20–35%.

Additionally, the paste may be formulated with silica gel or with silicates such as alkali metal and ammonium silicates, preferably sodium metasilicate in an amount of about 1–10% by weight. It is believed that gelatin forms a complex with metasilicate or silica gel via hydrogen bonding. ("The Colloid Chemistry Of Silica And Silicates" by Ralph K. Iler, p. 67, Cornell University Press, Ithaca, New York, 1955.) This complex enables the gelatin to withstand the heat generated by the revolving prophylaxis cup under actual conditions of use and, hence, imparts non-spattering properties to the paste.

The paste may also be made in a non-aqueous form to contain a mineral abrasive, a humectant, gelatin, a silicate or silica gel in an amount of about 1–10% by weight and an acid anhydride in the same amount. While sodium metasilicate is preferred, other water soluble silicates may also be used such as potassium metasilicate, sodium or potassium orthosilicates, disilicates, polysilicates, quaternary ammonium silicates, etc. Also, while succinic anhydride is preferred, other acid anhydrides may be used such as acetic, maleic, fumaric, etc.

I am aware that my co-worker James R. Mellberg has discovered that a non-aqueous prophylactic paste consisting essentially of an abrasive a humectant, a soluble alkaline silicate and an acid-forming agent, such as an anhydride, has a retarded gelling time so that the paste is sufficiently flowable to be poured through a nozzle under relatively low pressure into individual containers where it subsequently gels substantially void-free. Our common assignee has filed an application for patent on Mellberg's invention under Ser. No. 872,841, filed Jan. 26, 1978, which is copending with this application.

In my instant invention the anhydride reacts with the metasilicate to form silica gel which in turn combines with the gelatin to form the aforementioned complex that enables the gelatin to withstand the heat generated by the revolving prophylaxis cup.

The paste may also include the fluoride ion and, while the preferred fluoride compound is ammonium silicofluoride, other fluorides or fluoride-containing substances may be used such as $Na_2FPO_3$, $NaF$, $KF$, $LiF$, $SnF_2$, $SnF_4$, $SnZnF_6$, $NaTiF_5$, $Na_2SiF_6$, fluorozirconates, fluorostannites, fluoroborates, etc.

The following Tables contain non-limitative examples of dental prophylactic pastes with and without fluorides and including their viscosities. Table I contains examples of dental prophylactic pastes with and without fluoride in which medium pumice is the abrasive. Table II contains examples of dental prophylactic pastes containing fine pumice. Table III contains examples of dental prophylactic pastes with and without fluoride in which non-pumice abrasives are used.

TABLE I

| Paste Ingredients | % w/w | | | | | |
|---|---|---|---|---|---|---|
| | 1 | 2 | 3 | 4 | 5 | 6 |
| Pumice, medium | 40 | 45 | 50 | 40 | 45 | 50 |
| Glycerin | 28 | 28 | 28 | 30 | 30 | 30 |
| Gelatin (Type A, 300 Bloom Gms) | 1 | 1 | 1 | 2 | 2 | 2 |
| Sodium Metasilicate | 5 | 5 | 5 | — | — | — |
| Syloid 244 (Silica Gel) | — | — | — | 2 | 2 | 2 |
| Flavor | | | | 0.5 | 0.5 | 0.5 |
| Sorbitol Powder | | | | 2 | 2 | 2 |
| Color | | | | 0.02 | 0.02 | 0.02 |
| Potassium Sorbate (preserv.) | | | | 0.05 | 0.05 | 0.05 |
| Water, purified | 26 | 21 | 16 | 23.43 | 18.43 | 13.43 |

TABLE I-continued

| Paste Ingredients | % w/w | | | | | |
|---|---|---|---|---|---|---|
|  | 1 | 2 | 3 | 4 | 5 | 6 |
| Viscosity, cps at 35° C. | 1400 | 1500 | 6500 | 1250 | 5750 | 24,000 |

Syloid 244 silica gel is made by the Grace Chemical Company and ranges in particle size from 1–30 microns.

Sodium benzoate may also be used as a preservative instead of potassium sorbate.

The preferred procedure for making the pastes of Examples 1–3 containing sodium metasilicate is to dissolve the sodium matasilicate in the glycerin with warming, dissolve the gelatin in hot water, place the glycerin/metasilicate in a mixer, add the pumice, then add the gelatin/water and mix well until the mass is homogeneous, keeping the mixture at 40°–45° C.

The preferred procedure for making the pastes of Examples 4–6 containing silica gel is to add the gelatin to hot water and stir until dissolved, add the silica gel to the glycerin with rapid stirring and warming, combine the pumice, sorbitol, flavor, color and preservative in a mixer, add the gelatin/water to the glycerin/silica gel and mix well, add this mixture to the solids in the mixer and mix well until blended.

The viscosity was measured immediately after mixing using Brookfield Viscometer Model LVT, Spindle #4, Speed 12 rpm at 30°–40° C., generally at about 35° C. and recorded in centipoises (cps).

TABLE II

| Paste Ingredients | % w/w | | |
|---|---|---|---|
|  | 7 | 8 | 9 |
| Pumice, fine | 40 | 45 | 50 |
| Glycerin | 30 | 30 | 30 |
| Gelatin (Type A, 300 Bloom Gms) | 2 | 2 | 2 |
| Syloid 244 (Silica Gel) | 2 | 2 | 2 |
| Flavor | 0.5 | 0.5 | 0.5 |
| Sorbitol Powder | 2 | 2 | 2 |
| Color | 0.02 | 0.02 | 0.02 |
| Potassium Sorbate | 0.05 | 0.05 | 0.05 |
| Water, purified | 23.43 | 18.43 | 13.43 |
| Viscosity, cps at 35° C. | 4400 | 19,000 | 126,000 |

The preferred procedure to prepare the dental prophylactic pastes of Examples 7–9 is the same as that used to prepare the pastes of Examples 4–6 as set forth hereinbefore. The viscosity readings were made in the same way.

Fine pumice is available commercially, for example, from James H. Rhodes & Company of Chicago, Ill. 84% of its mass has an average particle diameter of less than 44 microns as compared to medium pumice in which 45% of its mass has an average particle diameter of less than 44 microns. Silica Ottawa 295 used as an abrasive in the examples which follow has an average particle diameter of 7.3 microns.

TABLE III

| Paste Ingredients | % w/w | | |
|---|---|---|---|
|  | 10 | 11 | 12 |
| Silica, Ottawa #295 (abrasive) | 50 | 60 | 60.00 |
| Glycerin | 30 | 20 | 8.00 |
| Syloid 244 (Silica Gel) | 2 | 2 | 2.00 |
| Flavor | 0.5 | 0.5 | 0.2600 |
| Sorbitol Powder | 2 | 2 | 10.000 |
| Color | 0.02 | 0.02 | 0.007 |
| Potassium Sorbate | 0.05 | 0.05 | 0.033 |
| Gelatin (Type A, 300 Bloom Gms) | 2 | 2 | 2 |
| Water, purified | 13.43 | 13.43 | 16.556 |
| Sodium biphosphate, N.F. | — | — | 0.418 |
| Phosphoric acid, 85% N.F. | — | — | 0.086 |
| Ammonium silicofluoride | — | — | 0.6400 |

TABLE III-continued

| Paste Ingredients | % w/w | | |
|---|---|---|---|
|  | 10 | 11 | 12 |
| Viscosity, cps at 35° C. | 3750 | 26,250 | 9400 |

Silica Ottawa 295 is ground silica which as a surface area ($cm^2$/gm) of 3332, an average particle diameter of 7.3 microns, a pH of 6.8, an oil absorption (lb/100 lb) of 22.9 and a water absorption (lb/100 lb) of 22.8.

The preferred procedure for making the dental prophy pastes of Examples 10 and 11 is to add the gelatin to hot water until dissolved, add the silica gel to the glycerin with rapid stirring and warming, combine the abrasive, sorbitol, flavor, color and preservative in a mixer, add the gelatin/water to the glycerin/silica, mix well and add the mixture to the solids in the mixer and mix until blended. The preferred procedure to make the fluoride-containing prophy paste of Example 12 is to dissolve the gelatin in half the amount of water, dissolving the potassium sorbate, sorbitol, sodium biphosphate, ammonium silicofluoride, phosphoric acid and color in the rest of the water, dissolving the silica gel in the glycerin with rapid stirring and warming and adding it to the gelatin solution. The abrasives and flavor are placed in a mixer and to this is added the solution of potassium sorbate, sorbitol, sodium biphosphate, ammonium silicofluoride, phosphoric acid and color and mixed well. The gelatin/water/silica gel/glycerin solution is then added and the entire mixture is mixed well for about 1 hour at about 40°–45° C. The viscosity was measured in the same manner as indicated hereinbefore at the midpoint between 30° and 40° C.

The preferred F- content is about 0.1 to 5.0% by weight, the gelatin 1–5% by weight and the silica gel 1–10% by weight; the pH of the paste is between 2.8 and 3.4.

I have also discovered that the addition of thickeners unaffected by temperatures above about 40° C. such, for example, as hydroxyethylcellulose or xanthan gum to the paste enhances the setting time thereof but does not impair the flowability (viscosity) of the paste (>40°). The thickeners are particularly useful in prophy pastes using silica abrasives and prevents their settling at elevated temperatures. The range of thickener concentration is 0.1 to 0.5%, preferably 0.25% by weight.

TABLE IV

| Paste Ingredients | % w/w | | |
|---|---|---|---|
|  | 13 | 14 | 15 |
| Silica Ottawa 295 | 55.0 | 55.185 | 55.20 |
| Glycerin | 8.00 | 8.00 | 8.00 |
| Sorbitol Powder | 10.00 | 10.00 | 10.00 |
| Syloid 244 (Silica Gel) | 1.50 | 2.00 | 2.00 |
| Keltrol (xanthan gum) | 0.25 | 0.25 | 0.25 |
| Gelatin (Type A, 300 Bloom Gms) | 1.50 | 1.50 | 1.50 |
| Flavor | 1.00 | 1.00 | 1.00 |
| Potassium sorbate | 0.05 | 0.05 | 0.05 |
| Color | 0.015 | 0.014 | 0.015 |
| Water, purified | 22.685 | 22.001 | 20.841 |
| Ammonium silicofluoride | — | — | 0.640 |

TABLE IV-continued

| Paste Ingredients | % w/w | | |
|---|---|---|---|
| | 13 | 14 | 15 |
| Sodium biphosphate, N.F. | — | — | 0.418 |
| Phosphoric acid, 85% N.F. | — | — | 0.086 |
| Viscosity, cps at 35° C. | 33,500 | 34,000 | 45,000 |

The preferred procedure for making the prophy pastes of Examples 13-15 is to disperse the silica gel in the glycerin, add the Keltrol in 7 ml of water, and the gelatin in 6 ml of hot water and the flavor, color and other solids in the rest of the water, except the sorbitol, abrasives and potassium sorbate which are placed in a mixer. The silica gel, Keltrol and the rest of the ingredients are then added and mixed well. The gelatin solution is added last and the entire mixture is blended to a substantially homogeneous mass.

The gelling agent in the prophy pastes of the instant invention is gelatin which enables the paste to be flowable at temperatures between 30° and 50° C. so that it can be pumped through nozzles at relatively low pressures into individual containers where it sets up to a vary thick consistency on standing. The abrasives used, i.e. pumice, silica, etc., influence the consistency and setting time of the paste.

As is evident from the examples in the Tables, generally an increase in the abrasive content increases viscosity, i.e. renders the prophy paste thicker and vice versa. The prophy pastes disclosed herein having a viscosity range of about 1200 to about 150,000 centipoises at 30°-40° C. are flowable through nozzles under relatively low pressures and are substantially non-spatterable in use by the dentist after setting.

In the article by Braden et al entitled "Rheology of Fluoride Gels", J.D.R., May-June 1974 which was cited in my parent application, six commercial fluoride gels were studied containing hydroxyalkyl cellulose thickening agents. They all showed that the apparent viscosity decreased (stress thinning) with shear rate and that the effect of temperature on viscosity was comparatively small.

It should first be noted that the topical fluoride gels studied by Braden et al are entirely different from the instant prophy pastes with and without fluorides. The fluoride gels are used primarily for topical application to children's teeth to prevent or retard caries, whereas a dental prophy paste is used primarily to remove tenacious stains and calculus. The addition of fluoride to dental prophy pastes enhances replacement of fluoride which is removed from the enamel during prophylactic treatment.

Secondly, the hydroxyalkyl cellulose thickeners of Braden et al have different properties from gelatin. These thickeners gel at elevated temperatures with continued heating whereas gelatin gels at room temperature or lower.

Thirdly, the differences in viscosity of the instant prophy pastes at 25° C. and 35° C. are marked and the pastes set to thicker consistencies with time, whereas the viscosities of the fluoride gels are not substantially changed by increase in temperature and remain as gels. They certainly cannot be used as dental prophy pastes and are not analogous in properties and functions to dental prophy pastes.

Like Braden et al, the Elbreder U.S. Pat. No. 3,337,412 was also cited in my parent application and deals with gels for topical application to teeth having a pH of 1.8 to 4.5, water, a water soluble fluoride, a water soluble phosphate and a gelling agent sufficient to impart a viscosity of 7,000 to 100,000 centipoises to the gel. The gelling agents disclosed in Elbreder are hydroxyethyl cellulose, carboxymethyl cellulose, magnesium aluminum silicate and silica aerogel. They are not gelatin or the preferred gelatin-silica gel or gelatin-metasilicate combination of the instant prophy paste. Moreover, Syloid 244 silica gel made by W. R. Grace & Co. is not the same as the silica aerogel referred to in Elbreder.

Additionally, silica abrasives and silica gel differ in properties. For example, the Ottawa silica and the Syloid 244 silica gel ingredients in several of the instant prophy pastes differ as follows: The silica is natural, the silica gel is synthetic; the average particle size in microns of the silica is 7.3, that for the silica gel is 4; the pH of the silica is 6.8, that for the silica gel is 7.6; the surface area (cm$^2$/gm) for silica is 3332, for the silica gel is $9.61 \times 10^{10}$; the oil absorption (lb/100 lb) is 22.9 for the silica, 305 for the silica gel; the water absorption (lb/100 lb) for the silica is 22.8, for the silica gel it is 150 and the hardness (Mohs scale) for the silica is 7, that for the silica gel is 5.

As indicated in my parent application, a commercial preparation is marketed as Nupro by Janar Company of Grand Rapids, Mich. under the Najjar U.S. Pat. No. 3,228,845 which discloses a prophylactic paste which combined about 50% pumice flour, about 20-25% glycerine, about 12% water, up to about 2% agar agar and about 10% sodium silicate which is claimed to flow evenly and be non-splattering in use. I have discovered that the use of gelatin instead of agar agar in a range by weight by about 0.01 to 10% improves the characteristics of flowability and non-spatterability of the Nupro paste. The following Tables V and VI include nonlimitative examples comparing equivalent pastes containing gelatin with those containing agar agar.

TABLE V

| Paste Ingredients | Agar Agar % w/w | | Gelatin % w/w | |
|---|---|---|---|---|
| Silica, Ottawa 295 (abrasive) | 50 | 60 | 50 | 60 |
| Glycerol | 30 | 20 | 30 | 20 |
| Syloid 244 (Silica Gel) | — | — | 2 | 2 |
| Sodium Metasilicate | 2 | 2 | — | — |
| Flavor | 0.5 | 0.5 | 0.5 | 0.5 |
| Sorbitol Powder | 2 | 2 | 2 | 2 |
| Potassium Sorbate | 0.05 | 0.05 | 0.05 | 0.05 |
| Color | 0.02 | 0.02 | 0.02 | 0.02 |
| Gelatin (Type A, 300 Bloom gms) | — | — | 2 | 2 |
| Agar Agar | 2 | 2 | — | — |
| Water, purified | 13.43 | 13.43 | 13.43 | 13.43 |
| Viscosity, cps at 35° C. | 97,000 | Too thick, dry, lumpy, non-homogeneous, no readings possible | 3750 | 26,250 |

TABLE VI

| Paste Ingredients | Agar Agar % w/w | Gelatin % w/w |
|---|---|---|
| Pumice, medium | 50 | 50 |
| Glycerol | 28 | 28 |
| Water | 16 | 16 |
| Sodium Metasilicate | 5 | 5 |
| Agar Agar | 1 | — |
| Gelatin (Type A, 300 Bloom gms) | — | 1 |
| Viscosity, cps at | Dry, lump, non- | 6500 |

TABLE VI-continued

| Paste Ingredients | Agar Agar % w/w | Gelatin % w/w |
| --- | --- | --- |
| 35° C. | homogeneous, no readings possible | |

The instant dental prophylactic paste combining gelatin or gelatin/silica gel or gelatin/soluble silicates in combination with abrasives having a viscosity range of 1200–150,000 centipoises at 30°–40° C. possesses superior flowability which allows it to be poured through a nozzle under relatively low pressure into individual containers wherein it forms solid discs or capsules at room temperature and which when applied to teeth by means of the cup mounted on a conventional motor driven dental tool will be substantially non-spattering.

What is claimed is:

1. A dental prophylactic paste which is substantially non-spattering and has improved flowability through a nozzle under low pressure comprising an abrasive, a humectant and gelatin, the abrasive being present in an amount by weight of about 30–80% and the gelatin being present in an amount by weight of about 0.01 to 10.0%, which is sufficient to impart to said composition a viscosity of between 1200 and 150,000 centipoises at a temperature between 30° and 40° C.

2. The dental prophylactic paste of claim 1 wherein the abrasive content is about 40–60% and the gelatin content is about 1–5%.

3. The dental prophylactic paste of claim 1 wherein the abrasive is a mineral compound and the humectant is a glycol.

4. The dental prophylactic paste of claim 1 wherein the abrasive is pumice and the humectant is glycerol.

5. The dental prophylactic paste of claim 1 and a fluoride compound present in an amount sufficient to provide a fluoride ion content of about 0.1 to 5.0% by weight.

6. The dental prophylactic paste of claim 1 and an alkali metal silicate in an amount of about 1–10% by weight.

7. The dental prophylactic paste of claim 1 and silica gel in an amount of about 1–10% by weight.

8. The dental prophylactic paste of claim 5 wherein the fluoride compound is ammonium silicofluoride.

9. The dental prophylactic paste of claim 1 and a thickener in an amount of 0.1 to 0.5% by weight.

10. A non-aqueous dental prophylactic paste which is substantially non-spatterable and has improved flowability through a nozzle under low pressure consisting essentially of an abrasive, a humectant, gelatin, a water soluble silicate and an acid anhydride, the abrasive being present in an amount by weight of about 30–80% and the gelatin in an amount of about 0.01 to 10.0%, which is sufficient to impart to said composition a viscosity of between 1200 to 150,000 centipoises at a temperature between 30° and 40° C.

11. The dental prophylactic paste of claim 10 wherein an alkali metal silicate is present in an amount of about 1–10% by weight and the anhydride is present in an amount of about 1–10% by weight.

12. The dental prophylactic paste in which the abrasive is present in about 40–60% by weight, the gelatin is present in about 1–5% by weight, sodium metasilicate is present in about 1–10% by weight and succinic anhydride is present in about 1–10% by weight.

* * * * *